United States Patent [19]

Jones

[11] 3,947,453

[45] Mar. 30, 1976

[54] 24-OXO-14a-AZA-D-HOMO-CHOLESTADIENE DERIVATIVES

[75] Inventor: Charles D. Jones, Indianapolis, Ind.

[73] Assignee: Eli Lilly and Company, Indianapolis, Ind.

[22] Filed: Sept. 6, 1974

[21] Appl. No.: 503,565

[52] U.S. Cl...... 260/287 AZ; 260/289 AZ; 424/258
[51] Int. Cl.² ........................................ C07D 215/06
[58] Field of Search.... 260/287 R, 287 AZ, 289 AZ

[56] References Cited
UNITED STATES PATENTS

| | | | |
|---|---|---|---|
| 2,738,350 | 3/1956 | Mazur................................ | 260/287 |
| 3,845,203 | 10/1974 | Williams et al..................... | 424/123 |

OTHER PUBLICATIONS

Tsuda et al., "J. Am. Chem. Soc.," 78, 4107-4111 (1956).

*Primary Examiner*—R. Gallagher
*Assistant Examiner*—David E. Wheeler
*Attorney, Agent, or Firm*—Charles W. Ashbrook; Everet F. Smith

[57] ABSTRACT

Side chain modification of 24-hydroxyimino-14a-aza-D-homo-cholesta-8(9), 14(14a)-dienes provides novel azasteroids having antifungal activities.

10 Claims, No Drawings

24-OXO-14a-AZA-D-HOMO-CHOLESTADIENE DERIVATIVES

BACKGROUND OF THE INVENTION

Infections having fungal origins constitute a large portion of human diseases caused by microorganisms. Several naturally occurring antibiotics and numerous synthetic compounds are currently available for treating fungal infections. Nystatin, a polyene antibiotic whose structural formula is not yet fully elucidated, in a commonly used antifungal agent which has met with good success. Even with the currently available antifungal agents however, there are still several diseases of fungal origin which are not easily controllable. Additionally, certain antifungal agents become ineffective with continued use due to the patient's sensitization to the particular drug. Consequently, the search for new antifungal agents and the therapy of fungal infections is the object of much laboratory and clinical investigation.

The isolation and characterization of novel 24-methylene-14a-aza-D-homo-cholestadienes which show good antifungal activity has recently been accomplished from cultures of a strain of *Geotrichum flavobrunneum*. This organism is described in detail by Miller et al., *Mycologia* 49, 779–808, 1957. The preparation and isolation of these novel azasteroids is the subject of co-pending U.S. patent application Ser. No. 327,171, filed Feb. 2, 1973, entitled ANTIBIOTIC A-25822 AND PROCESS FOR PREPARATION THEREOF, now U.S. Pat. No. 3,845,203.

The compounds provided by the present invention are in general prepared by modifying derivatives of the abovementioned naturally occurring 24-methylene-14a-aza-D-homo-cholestadienes. The compounds provided herein are useful as antifungal agents.

SUMMARY OF THE INVENTION

The compounds of this invention have the formula:

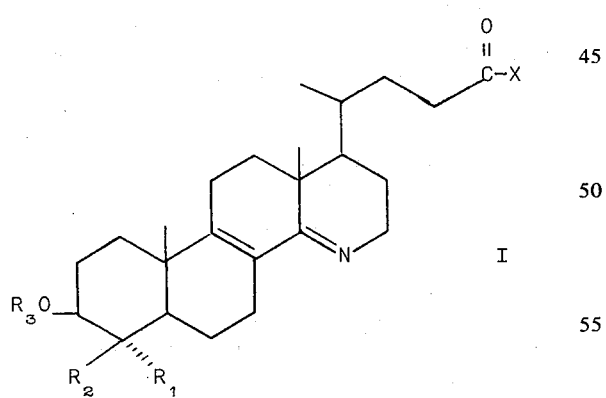

in which $R_1$ and $R_2$ are both hydrogen or both methyl; $R_3$ is hydrogen or $C_1-C_4$ alkanoyl; and X is $NR_4R_5$, $OR_6$, or halogen, wherein $R_4$ and $R_5$ independently are hydrogen or $C_1-C_4$ alkyl, and $R_6$ is hydrogen, $C_1-C_4$ alkyl, or an alkali metal cation. The pharmaceutically acceptable salts of the steroid-like compounds of this invention are included herein.

One object of the present invention is to provide new steroid-like compounds which are useful pharmacological agents, particularly for controlling diseases of fungal origin.

DETAILED DESCRIPTION OF THE INVENTION

This invention provides new organic acids, esters, and amides, which compounds have the general structural formula shown hereinabove.

As used herein, the term "$C_1-C_4$ alkanoyl" refers to carboxylic acid residues such as formyl, acetyl, propionyl, butyryl and isobutyryl. The term "$C_1-C_4$ alkyl" includes methyl, ethyl, isopropyl, butyl, isobutyl, and related groups. "Halogen" refers to fluorine, chlorine, bromine, and iodine.

The organic bases of this invention generally form pharamceutically acceptable salts with a variety of inorganic and strong organic acids. The particular acid used to form a salt with the bases of the invention is not critical; however, the salt formed should be substantially non-toxic to animal organisms. Typical acids commonly used in salt formation include hydrohalic acids such as hydrobromic, hydrochloric and hydroiodic acid, as well as acids such as sulfuric, phosphoric, sulfamic, acetic, formic, succinic, benzoic, ascorbic, maleic, and related acids. The organic bases of the invention additionally form quaternary immonium salts with any of a number of alkylating agents such as alkyl halides, sulfate and aromatic sulfonates. Examples of such agents include methyl chloride, ethyl iodide, dimethyl sulfate, methyl toluenesulfonate, and the like.

When X in the foregoing formula is $OR_6$ and $R_6$ is hydrogen, the new steroid-like compound is an acid. Such acids can be converted to the corresponding alkali metal salt when desired.

In general, the compounds of this invention can be prepared by acidic rearrangement of a hydroxyimino-aza-steroid of the formula

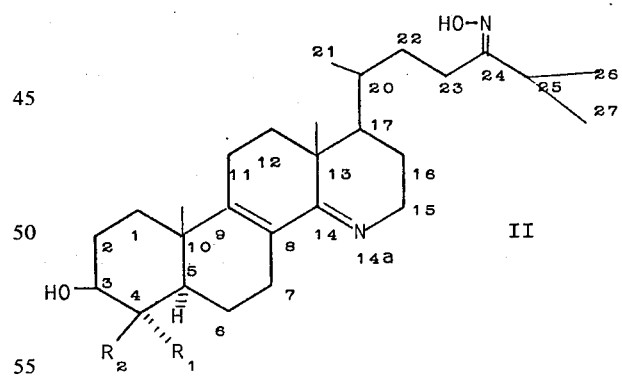

in which $R_1$ and $R_2$ are as defined hereinabove.

The new compounds of the present invention are named systematically as cholestane derivatives by following the numbering system shown in the above formula. A preferred starting material, wherein $R_1$ and $R_2$ in the above formula are both hydrogen, is named accordingly as 3β-hydroxy-24-hydroxyimino-14a-aza-D-homo-5α-cholesta-8(9), 14(14a)-diene. It will be understood that all of the compounds provided herein will have the same basic stereochemical configuration as the starting material. For example, the compounds described hereinbelow will have a 3-hydroxy group, or a 3-alkanoyloxy group, in the β-configuration as indicated by a solid bonding line between the carbon and oxygen atoms at $C_3$. Additionally, all of the compounds will have a hydrogen at $C_5$ in the α-configuration. By way of simplification, the terms α and β will be omitted from the systematic names used hereinafter throughout this application. For example, the preferred starting material named above will hereinafter be named 3-hydroxy-24-hydroxyimino-14a-aza-D-homo-cholesta-8(9), 14(14a)-diene.

In one aspect of this invention, the oxime of the above formula is subjected to strong acidic reaction conditions, thereby effecting a rearrangement to the corresponding amide. More specifically, treatment of the oxime with a suitable acid effects a Beckmann rearrangement to the corresponding isopropylamide, namely a 24-oxo-14a, 24a-diaza-D-homo-cholestadiene derivative. Suitable acids which are most commonly used to effect the rearrangement of the oxime include mineral acids such as hydrochloric, sulfuric, hydrobromic, phosphoric, nitric, or related acids; or organic acids such as formic acid, acetic acid, trichloroacetic acid, and the like. Agents such as phosphorus pentachloride can be incorporated if desired. The reaction can best be carried out in a solvent. Generally, the particular acid selected for the rearrangement is used in quantities sufficient to serve as the solvent for the reaction; however, co-solvents such as acetic anhydride, formic-acetic anhydride, dimethylformamide, dimethylsulfoxide, dioxane, or the like, can be utilized. In practice, the reaction is most conveniently carried out by stirring the oxime in an appropriate acid, such as formic acid or acetic acid for instance, without additional solvents. The rearrangement to the corresponding amide is normally complete after about 1 to 8 hours when the reaction is carried out at a temperature of about 25° to 125°C. The product is readily isolated by removal of the acidic solvent, for example by evaporation, and further purification can be accomplished by normal procedures, such as chromatography or crystallization for example, if needed. The product amide normally exists as the acylated derivative of the 3-hydroxy group, especially when an acid anhydride, such as acetic anhydride for example, was used as a solvent or co-solvent in the reaction mixture. When desired, such a 3-alkanoyloxy derivative can readily be converted to the corresponding 3-hydroxy derivative by mild basic hydrolysis, for example with aqueous sodium or potassium hydroxide. The 3-alkanoyloxy compound is generally treated with about a 1 molar amount of an aqueous base for about ½ to 1 hour at 20° to 30°C., thereby effecting hydrolysis to the corresponding 3-hydroxy derivative.

The amides of the invention are useful not only as antifungal agents but also as intermediates leading to a variety of other useful compounds. For example, an amide of this invention can be alkylated or acylated at the amide nitrogen, or alternatively the amide can be hydrolyzed to the corresponding acid with strong basic hydrolysis conditions. In particular, the amide provided by the rearrangement of the corresponding oxime is commingled with a strong base in a suitable solvent and stirred at a temperature of about 50° to 150°C. for a period of time of about 4 to 20 hours, thereby effecting cleavage of the amide group to the corresponding carboxylic acid derivative. Typical strong bases commonly used in the reaction include alkali metal hydroxides such as sodium hydroxide, potassium hydroxide, lithium hydroxide, and the like. Generally, the base is used in excess of the amide starting material, for example from about 2 to about 50 molar excess, or even more can be incorporated if desired. Suitable solvents for the reaction include ethers such as dioxane or diglyme, and alcohols such as ethanol or ethylene glycol for instance. The product can be isolated as the alkali metal salt of the acid by removal of the solvent and recrystallization, or alternatively, the free acid can be isolated by adding water to the reaction mixture and acidifying the aqueous reaction mixture with an acid such as hydrochloric acid, and extracting the product acid therefrom with a water immiscible solvent such as diethyl ether or ethyl acetate. If desired, the acid product can be converted to an acid addition salt of the 14a-aza group by the proper adjustment of the pH, or alternatively the acid product can be converted back to a salt of the acid, for example by the addition of a base such as sodium hydroxide, potassium bicarbonate, ammonia, triethylamine, or the like. The acids so formed are systematically named herein as 25,26,27-trisnor-14a-aza-D-homo-cholesta-8(9), 14(14a)-diene-24-oic acid derivatives.

Like the amides described hereinabove, the new organic acid derivatives of this invention are valuable as antifungal agents and additionally as intermediates for the preparation of the acid halides and esters of the invention. In particular, the carboxylic acid group can be esterified by treating the acid with essentially any alcohol, normally in the presence of a proton source such as a mineral acid for example. The preferred ester derivatives are those prepared with lower $C_1$-$C_4$ alkyl alcohols. Examples of commonly used alcohols for the esterification reaction include methanol, ethanol, isopropanol, n-butanol, and the like. The reaction generally is carried out by stirring the trisnor-14a-aza-D-homo-cholestadieneoic acid in an appropriate alcohol, such as methanol for example, and in the presence of an acid such as concentrated sulfuric acid or hydrochloric acid. The reaction is best carried out at a temperature of about 20° to about 100°C., and is normally complete after about 10 to 30 hours. The product, a lower alkyl 25,26,27-trisnor-14a-aza-D-homo-cholestadiene-24-oate, is conveniently isolated by removal of the solvent. Further purification can be accomplished if needed by standard methods such as chromatography or crystallization for instance.

The lower alkyl 25,26,27-trisnor-14a-aza-D-homo-cholestadiene-24-oates can alternatively be prepared by careful ozonolysis of the above-mentioned 24-methylene-14a-aza-D-homo-cholestadienes in the presence of an alcohol, such as methanol for example. More specifically, a 24-methylene-14a-aza-D-homo-cholestadiene is treated with 1 molar equivalent of ozone, with the appropriate alcohol serving as the reaction solvent and in the presence of an acid, such as a mineral acid for example. The ozonolysis is best carried out at a temperature below about −50°C., preferably at about −70° to −80°C. The reaction is substantially complete after about 5 to 25 minutes. Any unreacted ozone is generally decomposed by the addition of an agent such as sulfur dioxide to the reaction mixture, and the product ester, a lower alkyl 25,26,27-trisnor-14a-aza-D-homo-cholestadiene-24-oate, is normally isolated by removal of the solvent.

The 25,26,27-trisnor-14a-aza-D-homo-cholestadiene-24-oic acids can be converted to the corresponding acid halide by reaction with an agent such as an oxalyl halide, phosphorus halide, thionyl halide, and the like. Generally, the acid halides are formed by commingling the acid, or an alkali metal salt of the acid, with an excess of the appropriate halogenating agent. The reaction is normally carried out in a solvent such as benzene or dichloromethane, and at a temperature of about 20° to 50°C. The acid halides are especially useful as intermediates leading to the steroid-like antifungal agents of this invention. For example, the acid halides can be treated with an alcohol, such as methanol or isopropanol for example, thereby forming the corresponding ester. Additionally, the acid halide can be treated with an amine, such as ammonia, dimethylamine, isopropylamine, or the like, thereby providing the corresponding amide.

Examples of typical steroid-like compounds provided by this invention include:

3-Hydroxy-25,26,27-trisnor-14a-aza-D-homo-cholesta-8(9), 14(14a)-diene-24-oic acid;

3-Hydroxy-25,26,27-trisnor-14a-aza-D-homo-4,4-dimethylcholesta-8(9), 14(14a)-diene-24-oic acid;

Isopropyl 3-Hydroxy-25,26,27-trisnor-14a-aza-D-homocholesta-8(9), 14(14a)-diene-24-oate;

Methyl 3-formyloxy-25,26,27-trisnor-14a-azonia-14a-methyl-D-homo-cholesta-8(9), 14(14a)-diene-24-oate iodide;

Butyl 3-isobutyroxy-25,26,27-trisnor-14a-aza-D-homo-cholesta-8(9), 14(14a)-diene-24-oate;

3-Propanoyloxy-24-oxo-14a,24a-diaza-D-homo-cholesta-8(9), 14(14a)-diene;

3-Hydroxy-24-oxo-14a, 24a-diaza-24a-N-methyl-D-homo-cholesta-8(9), 14(14a)-diene;

3-Hydroxy-25,26,27-trisnor-24-oxo-14a,24a-diaza-D-homo-4,4-dimethyl-cholesta-8(9), 14(14a)-diene;

3-Hydroxy-25,26,27-trisnor-24-oxo-14a,24a-diaza 4,4,24a,24a, tetramethyl-D-homo-cholesta-8(9), 14(14a)-diene-14a-ium chloride;

3-Acetoxy-24-oxo-14a,24a-diaza-D-homo-cholesta-8(9), 14(14a)-diene-14a-ium acetate;

Sodium 3-hydroxy-25,26,27-trisnor-14a-aza-D-homo-cholesta-8(9), 14(14a)-diene-24-oate;

3-Butyryloxy-25,26,27-trisnor-14a,24a-diaza-24a-butyl-24a-ethyl-D-homo-cholesta-8(9), 14(14a)-diene-14a-ium bromide;

Potassium 3-hydroxy-25,26,27-trisnor-14a-aza-D-homo-4,4-dimethyl-cholesta-8(9), 14(14a)-diene-24-oate; and the like.

The starting materials generally required for preparing the compounds of this invention are 3-hydroxy-24-hydroxyimino-14a-aza-D-homo-cholesta-8(9), 14(14a)-dienes. These compounds can be prepared by oxidizing a naturally occurring 3-hydroxy-24-methylene-14a-aza-D-homo-cholesta-8(9), 14(14a)-diene to the corresponding 24-oxo derivative, and converting the ketone so formed to the oxime by reaction with hydroxylamine. The oxidation of the 24-methylene starting material is generally accomplished by reaction with osmium tetroxide to form what is believed to be the corresponding glycol, and further oxidizing the glycol to a ketone with an agent such as sodium periodate or potassium permanganate for example. A typical oxidation, for instance, comprises reacting 3-hydroxy-24-methylene-14a-aza-D-homo-cholesta-8(9), 14(14a)-diene with from about 0.1 to 1.0 molar amounts of osmium tetroxide. The reaction is generally carried out in a solvent, such as formic or acetic acid for example. The oxidation product is normally completely formed after about 5 to 10 minutes when the reaction is carried out at a temperature of about 20° to 30°C. The oxidation product so formed is normally not isolated, but is further oxidized to the desired ketone by reaction with an oxidizing agent such as sodium periodate. Typically, the oxidizing agent is added directly to the reaction mixture, generally in about 1 to 4 molar amounts. Oxidation to the desired ketone is usually complete after about 24 to 100 hours when the reaction is conducted at about 20° to 30°C. The product, a 3-hydroxy-24-oxo-14a-aza-D-homo-cholesta-8(9), 14(14a)-diene, is generally isolated by removal of any excess oxidizing agent and solvent, for example by filtration and evaporation, and further purification can be accomplished if desired by general methods such as chromatography, crystallization, and the like.

The starting material required to prepare the 24-oxo-derivative is a 24-methylene-14a-aza-D-homo-cholesta-8(9), 14(14a)-diene derivative and is obtained by culturing a strain of *Geotrichum flavo-brunneum*, NRRL 3862, which strain is in the permanent culture collection of the Agricultural Research Service, Northern Utilization Research and Development Division, Department of Agriculture, Peoria, Ill. The organism which is cultured was isolated by the standard serial dilution procedure from a soil sample collected in the Grand Teton National Park region of Wyoming. The organism is described in detail by Miller, et al., *Mycologia*, 49, 779–808, 1957. The preparation and isolation of the starting material used in the present invention is the subject of co-pending U.S. patent application Ser. No. 327,171, now U.S. Pat. No. 3,845,203 filed Feb. 2, 1973, and is carried out as described hereinbelow.

A culture of *Geotrichum flavo-brunneum* is grown under submerged aerobic conditions in a fermentation medium comprising carbohydrates, amino acids, and nutrient inorganic salts. The organism is grown for about three days at a temperature of about 20° to 35°C. After the fermentation is complete, the fermentation mycelium is extracted with a suitable organic solvent, such as ethyl acetate or amyl acetate for instance. Evaporation of the solvent from the combined organic extracts provides a mixture of compounds. The starting materials for the present invention are separated from the mixture by chromatography and crystallization.

The new compounds of the present invention are useful chemotherapeutic agents particularly because of their antifungal properties against microorganisms such as *Candida tropicalis* and *Candida albicans* for example. The compounds inhibit fungal growth when applied to environmental surfaces such as shower stalls, foot baths, exterior surfaces of wood, concrete, brick, or the like, as well as to skin surfaces affected by fungal growth. The compounds are most conveniently formulated for use as a solution or suspension with a suitable diluent, excipient, or carrier. Typical diluents and carriers include water, alcohol, glycols, and the like. Additionally, the compound can be formulated as a cream or ointment with suitable carriers such as hydrocarbon waxes, polyethylene glycol, or a cold cream base for example, thereby being suitably formulated for topical application to infected skin surfaces.

The preparation of the compounds provided herein is more fully described in the following detailed preparations and examples. It is to be understood, however, that the examples are provided to serve only as illustration of particular aspects of the invention, and are not to be construed as limiting the invention to the particular compounds or methods specifically described. The compounds described hereinbelow are characterized by typical nuclear magnetic resonance (nmr) absorptions, given in delta ($\delta$) values, mass spectral ($m/e$) parent molecular ion absorption (M+), and by melting point, and by characteristic infrared absorptions.

PREPARATION 1

The production of the starting materials required for the present invention is illustrated by the following procedures.

Spores of *Geotrichum flavo-brunneum* strain NRRL 3862 were inoculated on a nutrient agar slant having the following composition:

Agar Slant Medium

| Ingredient | Weight Volume (g./l.) |
|---|---|
| Glucose | 20 |
| Peptone | 5 |
| Potassium Dihydrogen Phosphate | 0.5 |
| Magnesium Sulfate | 0.02 |
| Ferrous Sulfate | 0.01 |
| Agar | 20 |

The above cultures were incubated at a temperature of 25°C. for 7 days. A loop of spores from the slant culture was transferred to a vegetative inoculum having the following composition:

Vegetative Medium

| Ingredient | Weight Volume (g./l.) |
|---|---|
| Sucrose | 25 |
| Edible Molasses | 36 |
| Corn Steep | 6 |
| Potassium Dihydrogen phosphate | 2 |
| NZ Case[1] | 2 |
| Tap Water | |

[1]Enzymatic digest of casein, Scheffield Chemical Co., Norwich, N.Y.

The inoculated vegetative medium was shaken on a rotary shaker at 250 r.p.m. for about 24 to 48 hours at a temperature of about 25°C. Five percent of the volume of the vegetative inoculum containing viable vegetative growth was employed to inoculate a fermentation medium having the following composition:

Fermentation Medium

| Ingredient | Weight/Volume (g./l.) |
|---|---|
| Glucose | 25 |
| Corn Starch | 10 |
| Peptone (meat) | 10 |
| NZ Amine A[1] | 4 |
| Molasses | 5 |
| Magnesium Sulfate Heptahydrate | 5 |
| Calcium Carbonate | 2 |
| Tap Water | |

[1]Pancreatic hydrolysate of casein, Scheffield Chemical Company, Norwich, N.Y.

The inoculated fermentation medium was agitated continuously for 72 hours at a temperature of 25°C. Throughout the fermentation, sterile air was passed through the fermentation medium at a rate of one half volume of air per volume of fermentation medium per minute.

Upon completion of the fermentation, the fermentation broth was extracted several times with ethyl acetate. The combined ethyl acetate extracts were concentrated to an oil residue. The residue was dissolved in a 20 percent acetone solution in n-hexane. Additional hexane was added to the mixture, and the solution was cooled to −20°C. whereupon 3-hydroxy-24-methylene-14a-aza-D-homo-cholesta-8(9), 14(14a)-diene crystallized. The crystals were collected by filtration and air dried, m.p. 115°–118°C. The filtrate was concentrated to dryness, providing an oily residue which was dissolved in a mixture of ethyl acetate-hexane-distilled water (80:16:4). The solution was passed over a column packed with basic alumina (Woelm grade W200, Water Associates, Inc., Framingham, Mass.). The column was eluted with the same solvent mixture, and eluate fractions of 1 liter volume each were collected. Eluate fractions 9 through 23 were combined and the solvent was removed therefrom under reduced pressure to provide a residue which was crystallized from acetone. The crystals were collected by filtration and identified as 3-hydroxy-24-methylene-14a-aza-D-homo-4,4-dimethyl-cholesta-8(9), 14(14a)-diene, m.p. 147°C.

PREPARATION 2

3-Hydroxy-24-oxo-14a-aza-D-homo-cholesta-8(9), 14(14a)-diene

A solution of 2 g. of 3-hydroxy-24-methylene-14a-aza-D-homo-cholesta-8(9), 14(14a)-diene in 80 cc. of an 80 percent aqueous acetic acid solution was stirred at 25°C. while 25 mg. of osmium tetroxide was added in one portion. The reaction mixture was stirred for five minutes, and 2.07 g. of sodium periodate was added to the reaction mixture. After stirring the reaction mixture at 25°C. for 72 hours, it was filtered and the solvent was removed from the filtrate, providing an oily residue. The residue was dissolved in 100 cc. of ethyl acetate and washed successively with aqueous sodium bicarbonate solution and with water, and dried. The solvent was removed under reduced pressure affording 1.5 g. of a crude product. The product was further purified by chromatography over a one inch by eight inch aluminum oxide column, eluting with ethyl acetate. The solvent was removed from the appropriate fractions affording 1.3 g. of 3-hydroxy-24-oxo-14a-aza-D-homo-cholesta-8(9), 14(14a)-diene as a crystalline solid. M.P. 70°–71°C., m/e: M+ 413 nmr (CDCl$_3$):
 $\delta$1.02, 3H, C-18 CH$_3$
 $\delta$1.00, 3H, C-19 CH$_3$
 $\delta$0.91, 3H, C-21 CH$_3$
 $\delta$1.08, 6H, C-26,27 CH$_3$

PREPARATION 3

3-Hydroxy-24-hydroxyimino-14a-aza-D-homo-cholesta-8(9),14(14a)-diene

A solution of 1.4 g. of 3-hydroxy-24-oxo-14a-aza-D-homo-cholesta-8(9), 14(14a)-diene in 25 cc. of pyridine containing 1.3 g. of hydroxylamine hydrochloride was stirred and heated at 100°C. for 24 hours. The reaction mixture was concentrated to dryness under reduced pressure providing a residue which was dissolved in 100 cc. of ethyl acetate, washed with water and dried. The solvent was removed under reduced pressure affording 1 g. of 3-hydroxy-24-hydroxyimino-14a-aza-D-homo-cholesta-8(9), 14(14a)-diene. m/e M+ 428.

nmr (CDCl₃):
δ1.02, 3H, C-18 CH₃
δ0.96, 3H, C-19 CH₃
δ0.99, 3H, C-21 CH₃
δ1.08, 6H, C-26,27 CH₃

EXAMPLE 1

3-Formyloxy-24-oxo-14a,24a-diaza-D-homo-cholesta-8(9), 14(14a)-diene

A solution of 520 mg. of 3-hydroxy-24-hydroxyimino-14a-aza-D-homo-cholesta-8(9), 14(14a)-diene in 30 cc. of 98 percent formic acid was stirred and heated at reflux under a nitrogen atmosphere for four hours. The reaction mixture was cooled to room temperature and the solvent was removed under reduced pressure providing a brown residue. The residue was dissolved in 100 cc. of methylene chloride and washed successively with aqueous sodium bicarbonate solution and dried. Removal of the solvent under reduced pressure provided 3-formyloxy-24-oxo-14a,24-a-diaza-D-homo-cholesta-8(9), 14(14a)-diene. *m/e:* M+ 428.

nmr (CDCl₃):
δ1.04, 3H, C-18 CH₃
δ1.01, 3H, C-19 CH₃
δ0.95, 3H, C-21 CH₃
δ1.16, 6H, C-26,27 CH₃
δ5.4, 1H, 24a-NH

EXAMPLE 2

3-Hydroxy-25,26,27-trisnor-14a-aza-D-homo-cholesta-8(9), 14(14a)-diene-24-oic acid A suspension of 100 mg. of 3-formyloxy-24-oxo-14a,24a-diaza-D-homo-cholesta-8(9), 14(14a)-diene in 1 cc. of ethylene glycol was stirred at room temperature while 200 mg. of powdered potassium hydroxide was added in one portion. The reaction mixture was heated at reflux for 12 hours. The reaction mixture was cooled to about 25°C. and 50 cc. of water was added. The aqueous reaction mixture was extracted with diethyl ether and then acidified to pH 2 by the addition of 1N hydrochloric acid. The acidic aqueous solution was extracted with three 25 cc. portions of chloroform which had been warmed to about 35°C. The organic extracts were combined and dried and the solvent was removed under reduced pressure, providing 3-hydroxy-25,26,27-trisnor-14a-aza-D-homo-cholesta-8(9), 14(14a)-diene-24-oic acid, as the hydrochloride salt *m/e:* M+ 387.

IR (KBr): 1700–1720 cm⁻¹

EXAMPLE 3

Methyl 3-hydroxy-25,26,27-trisnor-14a-aza-D-homo-cholesta-8(9), 14(14a)-diene-24-oate A solution of 43 mg. of 3-hydroxy-25,26,27-trisnor-14a-aza-D-homo-cholesta-8(9), 14(14a)-diene-24-oic acid in 20 cc. of methanol containing about 3 percent gaseous hydrogen chloride was stirred at 25°C. for 16 hours. The reaction mixture was filtered through 2 g. of sodium bicarbonate and the solvent was removed from the filtrate under reduced pressure to provide methyl 3-hydroxy-25,26,27-trisnor-14a-aza-D-homo-cholesta-8(9), 14(14a)-diene-24-oate. *m/e:* M+ 401. IR (CHCl₃): 1745 cm⁻¹ nmr (CDCl₃):
δ1.00, 3H, C-19 CH₃
δ1.02, 3H, C-18 CH₃
δ3.70, 3H, —COOCH₃

EXAMPLE 4

Methyl 3-hydroxy-25,26,27-trisnor-14a-aza-D-homo-cholesta-8(9), 14(14a)-diene-24-oate A solution of 206 mg. of 3-hydroxy-24-methylene-14a-aza-D-homo-cholesta-8(9), 14(14a)-diene in 150 cc. of methanol was stirred and cooled to −78°C. in a dry ice-acetone bath. To the cold reaction solution was added 0.5 cc. of 1N hydrochloric acid and 0.5 millimoles of ozone gas. The reaction mixture was stirred for 10 minutes at −78°C., after which time sufficient sulfur dioxide was added to decompose any excess ozone remaining in the reaction mixture. The solvent was removed under reduced pressure, leaving an oily residue which was dissolved in 100 cc. of ethyl acetate and filtered through 2 g. of sodium carbonate. The solvent was removed from the filtrate under reduced pressure to afford 150 mg. of methyl 3-hydroxy-25,26,27-trisnor-14a-aza-D-homo-cholesta-8(9), 14(14a)-diene-24-oate as a pale yellow foam. *m/e:* M+ 401.

I claim:
1. The compound of the formula

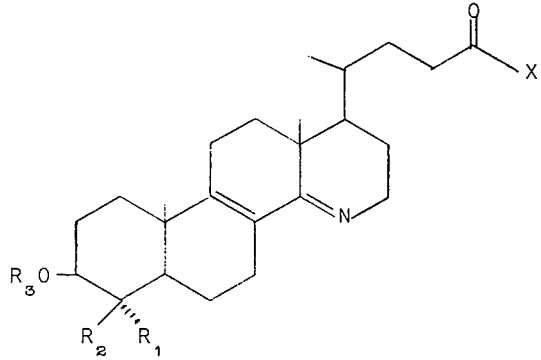

wherein:
R₁ and R₂ are both hydrogen or both methyl:
R₃ is hydrogen or C₁–C₄ alkanoyl;
X is halogen, NR₄R₅, or OR₆, wherein R₄ and R₅ independently are hydrogen or C₁–C₄ alkyl; R₆ is hydrogen, C₁–C₄ alkyl, or an alkali metal cation; and the pharmaceutically acceptable salts thereof.
2. The compound of claim 1 wherein R₁ and R₂ are both hydrogen.
3. The compound of claim 2 wherein R₃ is hydrogen.
4. The compound of claim 3 wherein X is NR₄R₅.
5. The compound of claim 4 wherein R₄ is hydrogen.
6. The compound of claim 5 wherein R₅ is isopropyl.
7. The compound of claim 3 wherein X is OR₆.
8. The compound of claim 7 wherein R₆ is hydrogen.
9. The compound of claim 7 wherein R₆ is methyl.
10. The compound of claim 1 wherein R₃ is other than hydrogen and X is NR₄R₅.

* * * * *